US006884069B2

(12) United States Patent
Goldman

(10) Patent No.: US 6,884,069 B2
(45) Date of Patent: Apr. 26, 2005

(54) ORAL CARE DEVICE

(75) Inventor: Paul Goldman, Marlboro, MA (US)

(73) Assignee: The Gillette Company, Boston, MA (US)

( * ) Notice: Subject to any disclaimer, the term of this patent is extended or adjusted under 35 U.S.C. 154(b) by 160 days.

(21) Appl. No.: 09/904,415

(22) Filed: Jul. 12, 2001

(65) Prior Publication Data

US 2003/0013063 A1 Jan. 16, 2003

(51) Int. Cl.⁷ .............................................. A61C 3/02
(52) U.S. Cl. ...................................................... 433/88
(58) Field of Search ..................... 433/80, 88; 601/162, 601/163, 164, 165

(56) References Cited

U.S. PATENT DOCUMENTS

| 1,664,369 A | 3/1928 | Maurer |
| 2,661,537 A | 12/1953 | Angell |
| 2,696,049 A | 12/1954 | Black |
| 2,759,266 A | 8/1956 | Cassani |
| 2,813,529 A | 11/1957 | Ikse |
| 3,134,127 A | 5/1964 | Klein |
| 3,164,153 A | 1/1965 | Zorzi |
| 3,496,933 A | 2/1970 | Lloyd ........................... 128/66 |
| 3,578,884 A | 5/1971 | Jacobson ................... 417/317 |
| 3,823,710 A | 7/1974 | Borden ......................... 128/40 |
| 3,971,136 A * | 7/1976 | Madsen ........................ 433/88 |
| 3,972,123 A | 8/1976 | Black |
| 4,174,571 A | 11/1979 | Gallant ....................... 433/216 |
| 4,214,871 A | 7/1980 | Arnold ....................... 433/216 |
| 4,236,889 A * | 12/1980 | Wright ......................... 433/86 |
| 4,322,207 A * | 3/1982 | Madsen ....................... 433/216 |
| 4,412,402 A | 11/1983 | Gallant ......................... 51/439 |
| 4,422,450 A | 12/1983 | Rusteberg .................... 128/62 |
| 4,522,597 A | 6/1985 | Gallant ....................... 433/216 |
| 4,540,365 A | 9/1985 | Nelson et al. ................ 433/88 |
| 4,595,365 A | 6/1986 | Edel et al. .................. 433/216 |
| 4,696,644 A | 9/1987 | Goof ............................ 433/88 |
| 4,735,200 A | 4/1988 | Westerman .................. 128/66 |
| 4,776,794 A | 10/1988 | Meller ......................... 433/216 |
| 4,863,302 A | 9/1989 | Herzfeld et al. ............ 401/289 |
| 4,903,688 A * | 2/1990 | Bibby et al. .................. 433/80 |
| 4,906,187 A * | 3/1990 | Amadera ...................... 433/80 |
| 4,941,459 A | 7/1990 | Mathur ........................ 128/66 |
| 4,950,160 A | 8/1990 | Karst ........................... 433/88 |
| 5,062,795 A | 11/1991 | Woog ........................... 433/80 |
| 5,098,291 A | 3/1992 | Curtis et al. ................. 433/89 |
| 5,203,698 A * | 4/1993 | Blake et al. .................. 433/88 |
| 5,295,832 A | 3/1994 | Evans ......................... 433/216 |
| 5,387,182 A * | 2/1995 | Otani ........................... 601/165 |
| 5,393,228 A | 2/1995 | Policicchio .................. 433/88 |
| 5,503,553 A * | 4/1996 | Hines ........................... 433/80 |
| 5,593,304 A * | 1/1997 | Ram ............................ 433/82 |
| 5,746,595 A | 5/1998 | Ford ............................ 433/80 |
| 5,820,373 A | 10/1998 | Okano et al. ................. 433/80 |
| 6,179,614 B1 | 1/2001 | Elrod et al. ................... 433/88 |
| 6,217,327 B1 * | 4/2001 | Bedi ............................ 433/80 |
| 6,264,119 B1 * | 7/2001 | Truong ........................ 239/310 |
| 6,375,459 B1 * | 4/2002 | Kamen et al. ................ 433/80 |

FOREIGN PATENT DOCUMENTS

DE 19704567 2/1998 ............ A61C/3/02

OTHER PUBLICATIONS

Microprophy™ Owner's Manual, Danville Engineering, Inc., 2021 Omega Road, San Ramon, CA 94583, Instructions on Installation, abrasives, use, sterlization, Extended handpiece.

* cited by examiner

Primary Examiner—Cary E. O'Connor
(74) Attorney, Agent, or Firm—David A. Howley

(57) ABSTRACT

An oral care device includes an electric motor, an air compressor operated by the motor, and an enclosed container for holding a slurry. A first conduit conducts compressed air from the compressor into the container. The compressed air is at a pressure of between about 20 psi to about 50 psi. A second conduit conducts the slurry and air from the container to an applicator from which the slurry and air is sprayed into the oral cavity of a human. The second conduit is at least about 24 inches in length.

18 Claims, 11 Drawing Sheets

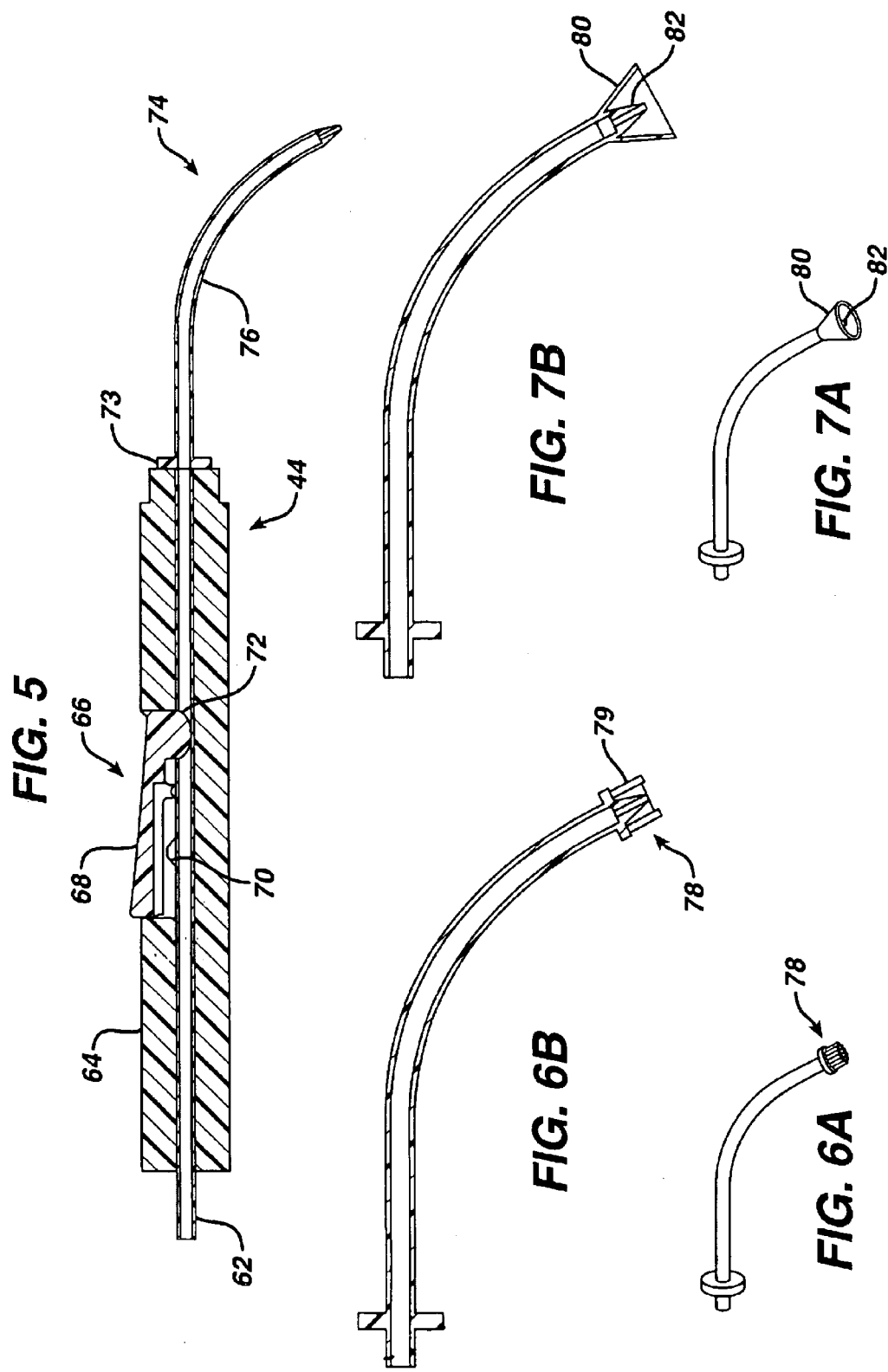

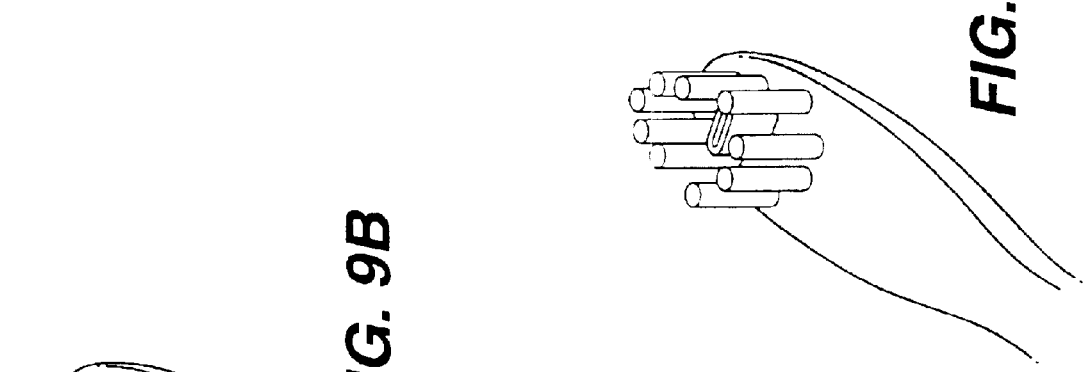
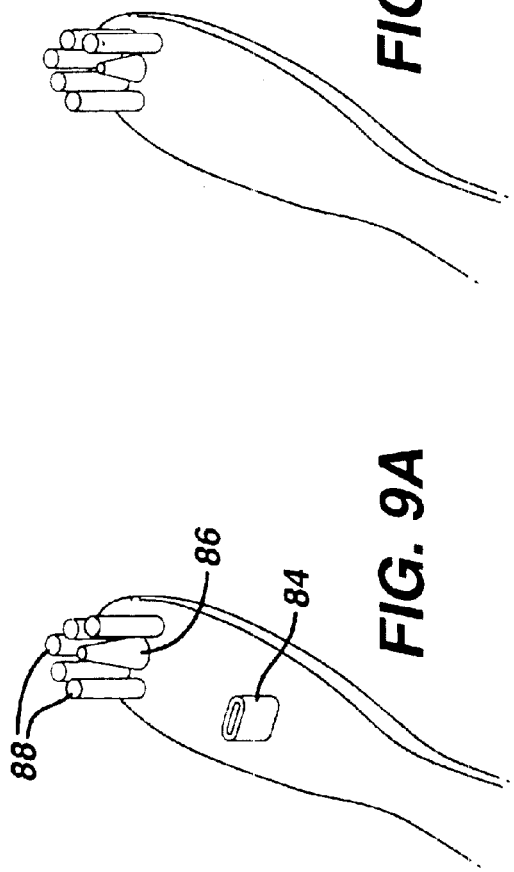
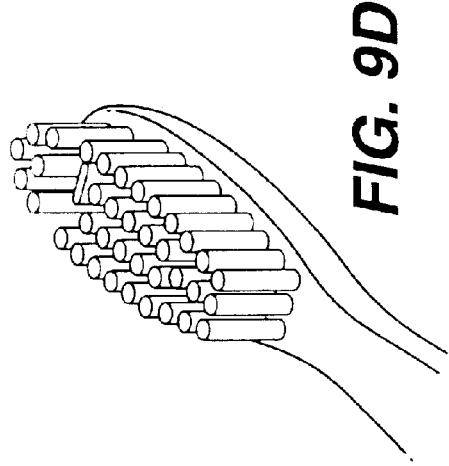
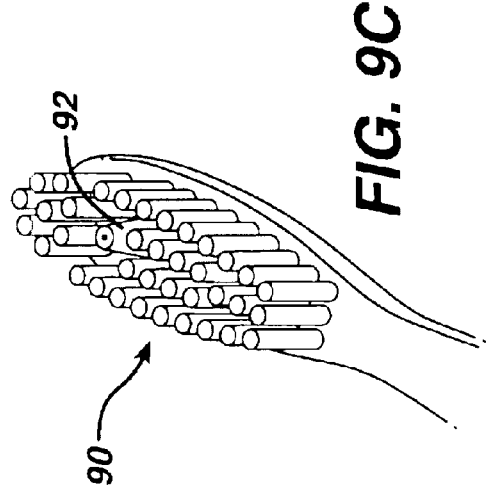

ORAL CARE DEVICE

FIELD OF THE INVENTION

The invention relates generally to the field of oral care, and in particular to devices which spray a fluid into a human oral cavity for cleaning purposes.

BACKGROUND OF THE INVENTION

U.S. Pat. No. 5,203,698 discloses a wet foam sandblaster used for oral care. A bubble foam laden with abrasive particles is propelled through a small nozzle by gas pressure. The system has very specific applications in the dental industry for 1) general cleaning of teeth such as removal of tobacco, tea and other stains; 2) for selectively abrading away carious enamel, 3) cleaning prosthodontic restorations, 4) abrading various tooth and restorative materials in preparation for bonding, and 5) periodontal pocket cleaning with osteophylic abrasives; and 6) cleaning of occlusal pits and fissures for sealing. In addition, the system has numerous applications in cleaning and etching materials in the jewelry, semi-conductor, automotive and other industries.

The apparatus for cleaning teeth and other surfaces comprises a canister capable of being sealed and pressurized, and receiving a mixture of liquid, abrasive particles and wetting agent. The canister also has a means to receive a stream of pressurized gas, a means to disperse pressurized gas into the mixture of liquid, abrasive particles and wetting agent thereby causing a formation of foam and urging the abrasive particles to become entrained into the foam. Also provided are a means to direct the abrasive laden foam to the surface to be cleaned, and a means to control the flow of the abrasive laden foam.

The product shown in the '698 patent is sold by Danville Engineering of San Ramon, Calif. This product is designed for use by a dental professional in a dentist office and not for home use by individual consumers. As such, some of the features of the product make it not suitable for home use. For example, the Danville product does not include an integral air compressor and electric motor to run the compressor. Accordingly, a consumer would have to buy a separate air compressor and place it in their bathroom along with the Danville product in order to use the system. Such an arrangement is inconvenient and would clutter up the bathroom counter.

Additionally, the Danville product is operated at an air pressure of 40–60 psi for light cleaning. However, when the extended handpiece is used on the product, the air pressure needed is at the upper end of the 40–60 psi range (assumed to be about 55–60 psi). While this pressure range (55–60) is safe when the product is being used by a dental professional on a patients teeth, it could be too high to be safely used by an individual in their home.

In order for the Danville product to accomplish certain functions, it is designed to be operated with a slurry having a volumetric ratio of 2 parts water to one part powder. Such a slurry represents an aggressive concentration that should preferably be administered by a dental professional and not a consumer during home use.

Air Force Inc. of Holland, Mich. sells a product called the Dental Air Force. This system uses air mixed with water and dental cleaner (sodium bicarbonate) to remove food and plaque off the teeth. Air delivers cleaner into tiny spaces between teeth and along the gums. Air and cleaner are sprayed from the end of a slim tip to remove plaque from the oral cavity.

A drawback to this system is that every time it is used, a portion of the hand-piece must be opened up, a new cup of dental cleaner must be inserted into the hand-piece, and then the portion of the hand-piece is reattached. This operation is inconvenient. Further, the operator must wait 20–30 seconds for the cup to fill with water before the unit can be used to clean the teeth. This is yet another inconvenience. Further, because the powder is placed in the hand-piece, the hand-piece is relatively large, thus making it awkward to use.

Deldent Ltd discloses a series of dental products which appear to be for use by dental professionals and not by people in their homes. This company sells several air polishing units which the company claims operates at 35 psi.

SUMMARY OF THE INVENTION

The present invention is directed to overcoming one or more of the problems set forth above. Briefly summarized, according to one aspect of the present invention, an oral care device includes a toothbrush having a head and one or more bristles extending from the head. A conduit is provided for supplying water, particulate and pressured air to the head such that the water, particulate and pressured air can be sprayed onto the teeth from the head to enhance cleaning. As such, the benefits of spray cleaning and possibly brushing the teeth are provided. Further, the bristles act as a guide in positioning the head, and the overall oral care device is compact and easy to use.

According to a second aspect of the invention, an oral care device includes a housing having an electric motor within the housing, and an air compressor within the housing that is operated by the motor. An enclosed container is attached to the housing and is used for holding a slurry. A first conduit conducts compressed air from the compressor into the container. A second conduit conducts the slurry and air from the container to an applicator from which the slurry and air is sprayed into the oral cavity of a human. By having the electric motor, compressor and container all associated with the housing, an apparatus is provided which is convenient for home use.

According to a third aspect of the invention an oral care device comprises an electric motor, an air compressor operated by the motor, and an enclosed container for holding a slurry. A first conduit conducts compressed air from the compressor into the container. The compressed air is at a pressure of between about 20 psi to about 50 psi. A second conduit conducts the slurry and air from the container to an applicator from which the slurry and air is sprayed into the oral cavity of a human. The second conduit is at least about 24 inches in length. By operating the device at an air pressure of between about 20 psi to about 50 psi when an applicator is used that is 2 or more feet from the container, teeth cleaning can be accomplished in the home in a safe manner without causing damage in the oral cavity.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 5 is a sectional view of the applicator 44 of FIG. 2;

FIG. 6A is a perspective view of an alternative nozzle design;

FIG. 6B is a sectional view of the nozzle of FIG. 6A;

FIG. 7A is a perspective view of a further alternative nozzle design;

FIG. 7B is a sectional view of the nozzle of FIG. 7A;

FIGS. 9A–E are perspective views of various head designs for the head of applicator 24;

DETAILED DESCRIPTION OF THE INVENTION

Figure 1:
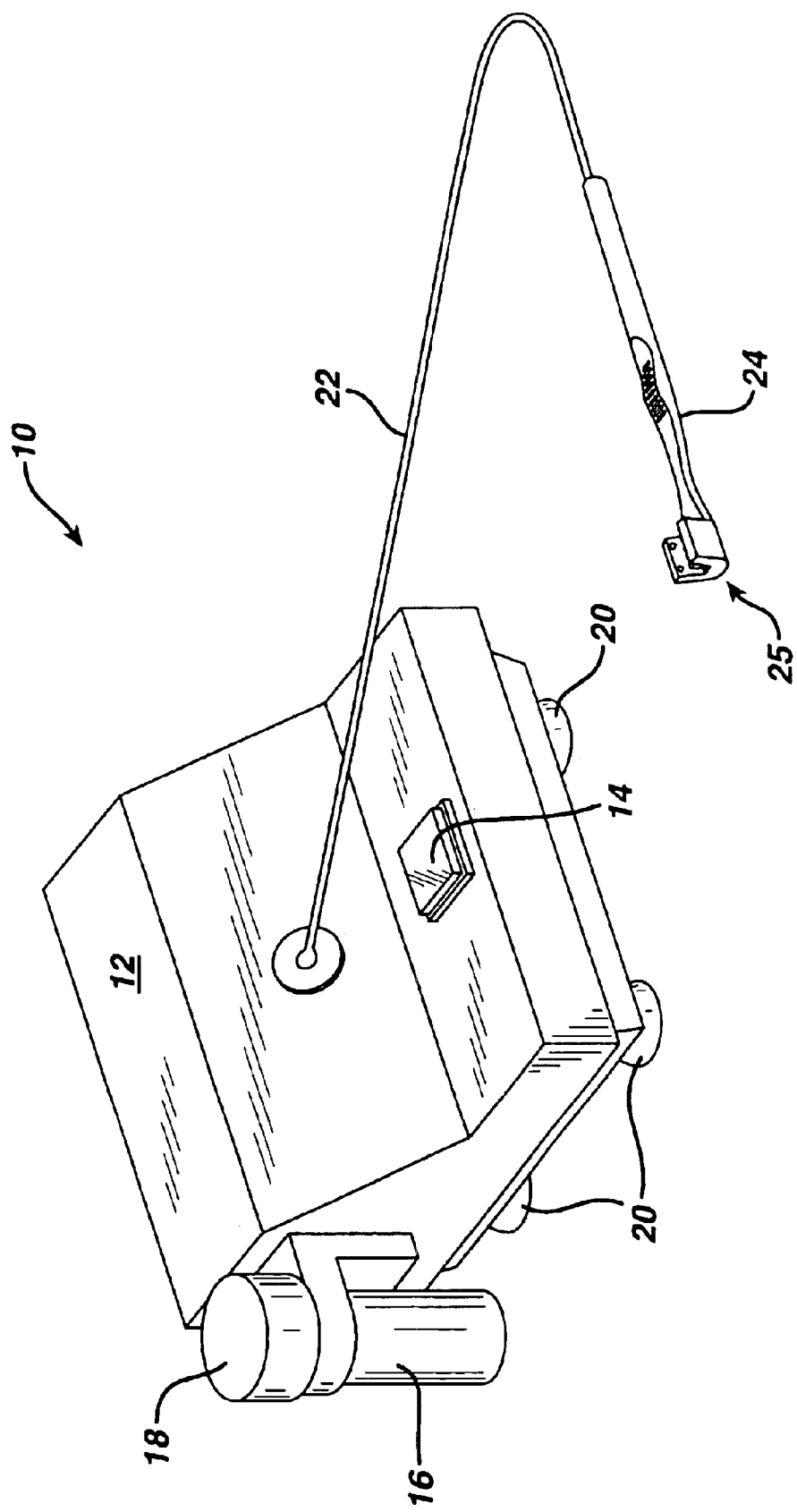
FIG. 1 is a perspective schematic view of an oral care device.

As shown in FIG. 1, an oral care device 10 includes a housing 12. A push-button 14 is used to turn the device on and off. A slurry reservoir 16 is detachably secured to housing 12 and includes an air-tight screw on top 18 which may use an o-ring to seal the container. The reservoir contains a slurry of water and abrasive powder (e.g. a particulate such as sodium bicarbonate and sodium laurel sulfate . . . a foaming agent). Other agents can be added to the slurry to perform various functions. For example, fluoride can be added to prevent cavities, hydrogen peroxide can be added to whiten teeth, and mint flavoring can be added to freshen breath. A set of four rubber feet 20 (one is not visible) resists sliding of the device on a bathroom counter. A hollow, flexible plastic tube 22 connects a spray applicator 24 to device 10. The water, air and particulate are sprayed from the applicator head 25 into the human oral cavity for cleaning purposes.

Figure 2:
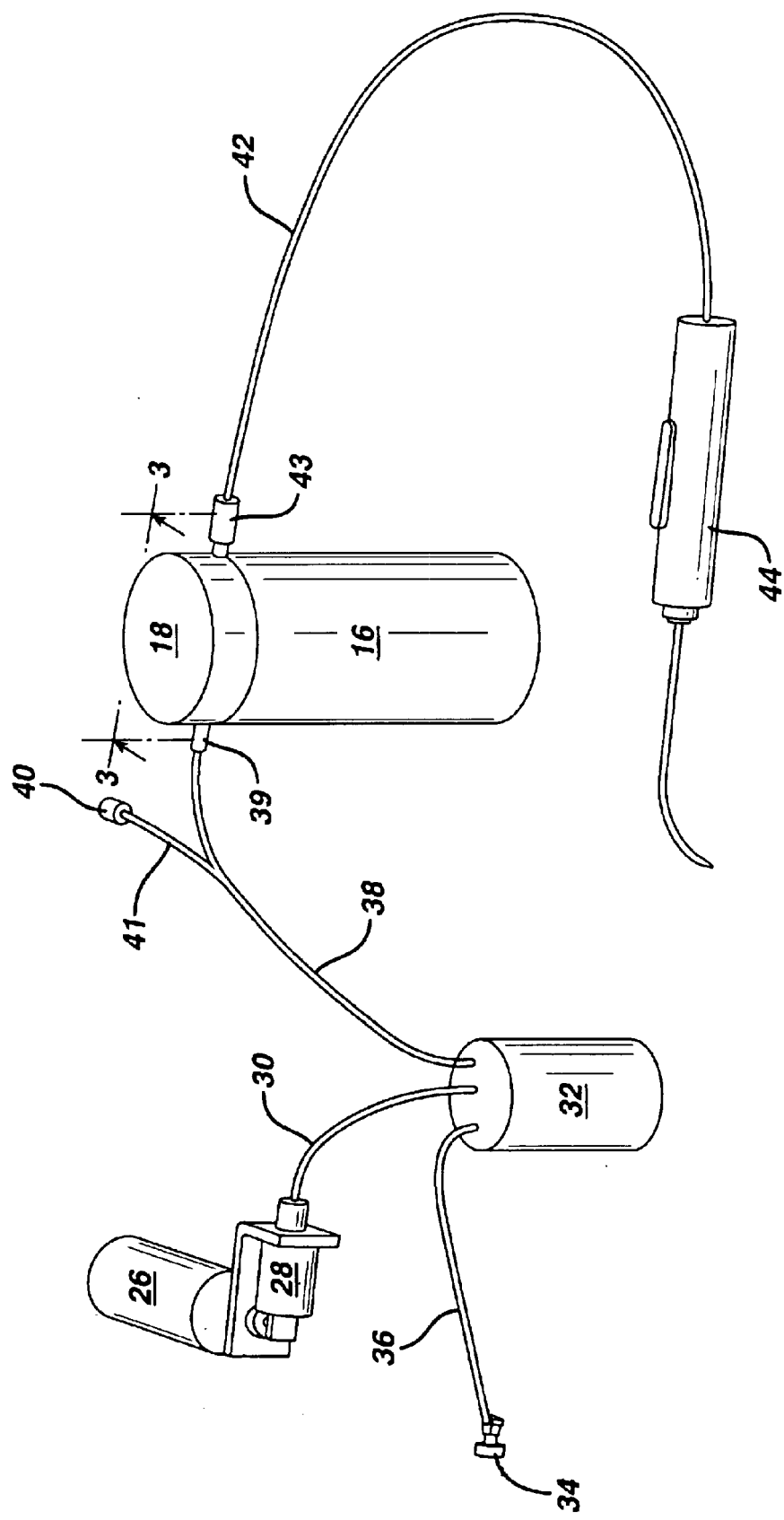
FIG. 2 is a schematic view of the operational elements of the device of FIG. 1.

Turning to FIG. 2, the operation of the oral care device will be described in more detail. An electric motor 26 is connectable to a power supply (e.g. 110 v 60 hz) by an electrical power cord (not shown). The motor is connected to and operates an air compressor 28. The compressor supplies compressed air to a tube 30 at a pressure of between about 20 psi to about 50 psi.

The compressed air exits tube 30 into an air ballast 32 which is used to smooth out the air pressure in the system. An adjustable valve 34 is connected to the air ballast by a tube 36. The adjustable valve can allow air to escape from the device in order to fine tune the air pressure in the system. Valve 34 can be replaced with an automatic pressure regulator. A tube 38 conducts compressed air from air ballast 32 to an inlet 39 of slurry reservoir 16. An over-pressure valve 40 is connected to tube 38 by a tube 41 and will open in the event the air pressure exceeds a pre-set limit. Air, water and particulate exit reservoir 16 via an outlet 43 into a tube 42 which conducts the mixture to an applicator 44 (different from applicator 24 of FIG. 1).

Figure 3:
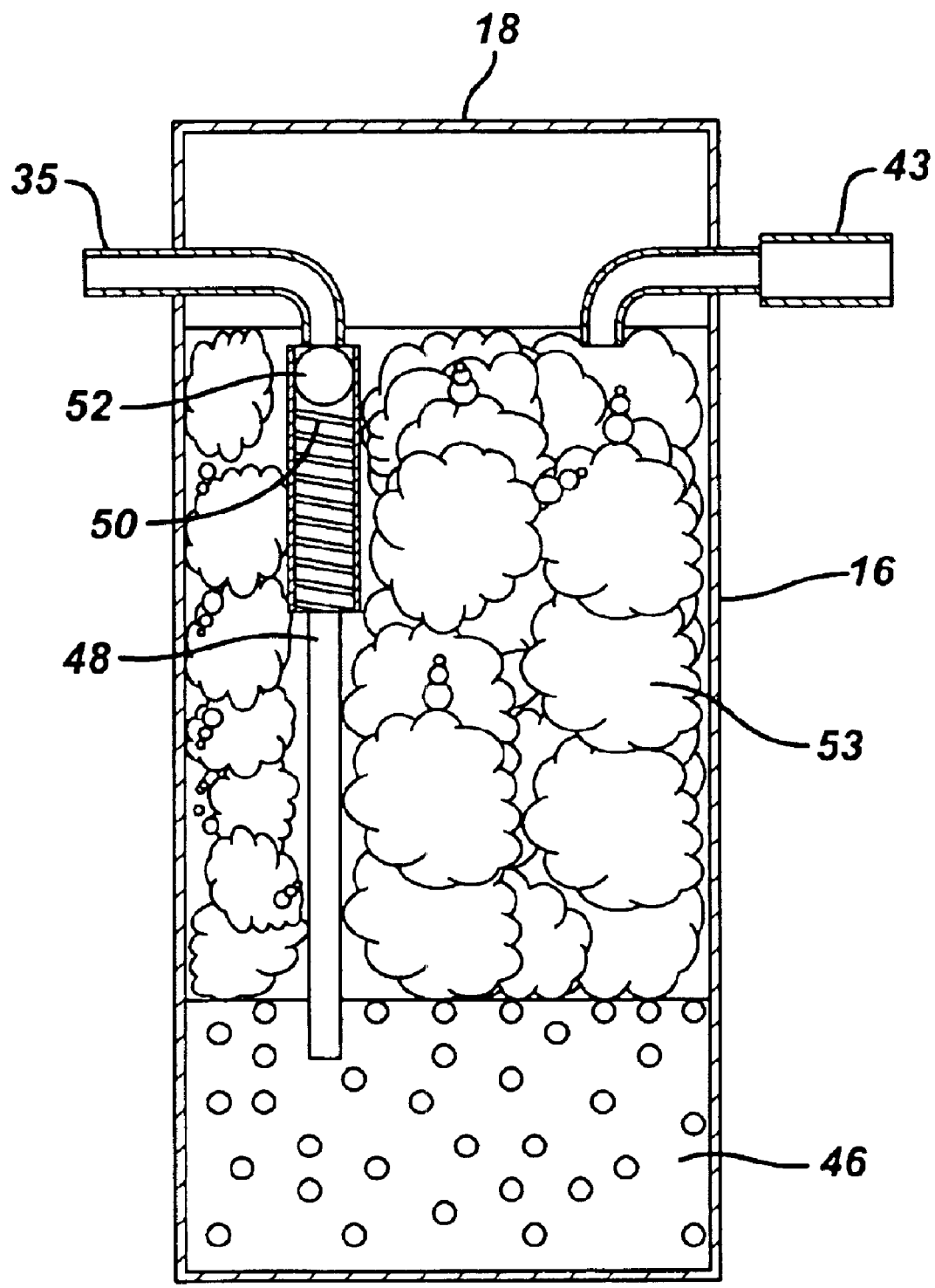
FIG. 3 is a sectional view of reservoir 16 of FIG. 2 looking along the direction of lines 3—3.
Figure 4:
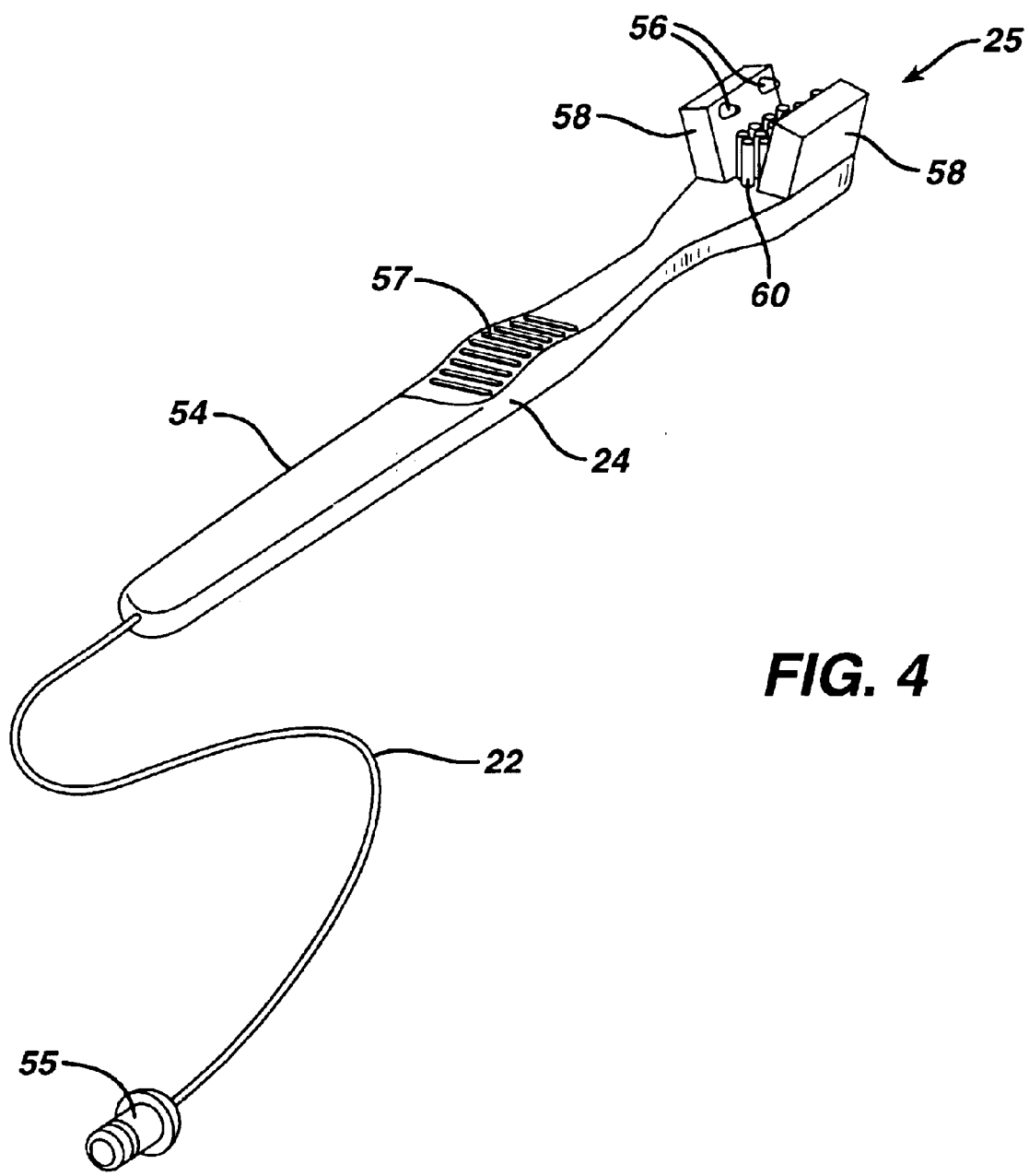
FIG. 4 is a perspective view of the applicator 24 of FIG. 1.

Referring to FIG. 3, reservoir 16 holds a slurry 46 (in FIGS. 2 and 3, top 18 has about the same diameter as reservoir 16, whereas in FIG. 1, top 18 has a larger diameter than the reservoir). The ratio of the particulate to the water by volume in the slurry is between 1:10 to 4:10, and preferably about 2:10. Compressed air enters the slurry by a tube 48 which is connected to inlet 35. A check valve includes a compression spring 50 which urges a ball 52 away from the spring to close off inlet 35 when the air pressure drops below a pre-set limit. This arrangement prevents possible back flow of the slurry into inlet 35 and beyond. Tube 48 extends to near the bottom of reservoir 16 and allows the compressed air to enter the slurry. The air agitates the slurry, creating bubbles and keeping the particulate in suspension. The air bubbles, laden with water and particulate, rise away from the top surface of the slurry as a bubble foam 53 (see U.S. Pat. No. 5,203,698 for more details). The continuing air pressure into reservoir 16 forces the air, water and particulate through outlet 43 and tube 42 to the applicator. FIG. 4 discloses applicator 24 from FIG. 1. Again, the applicator is connected to the slurry reservoir by a flexible tube 22. A fitting 55 secures the tube to outlet 43 of reservoir 16. Tube 22 forms part of a conduit for guiding the air, water and particulate from reservoir 16 to head 25 of the applicator. An on/off flow switch 57 is pressed to allow flow of the air, water and particulate to head 25 and released to disallow flow. The conduit extends through a handle 54 of the applicator to head 25. The conduit then splits and passes through a pair of manifolds 58 which each support a pair of nozzles 56 (only 1 pair is clearly visible). Within each manifold 58 the conduit splits again and connects to the two nozzles on the manifold. The air, water and particulate is ejected from the nozzle(s) in a way to safely remove plaque without damaging any hard or soft oral tissue. A plurality of bristle tufts 60 are also secured to head 25. The bristle tufts are primarily used to guide the placement of nozzles 56 within the mouth, but the bristles can also be used to simultaneously brush the teeth. Accordingly, air, water and particulate can be sprayed primarily onto the teeth and gums to provide enhanced cleaning.

Other means can be used to keep the particulate in suspension in addition to pressurized air. For example, a mechanical device such as an impeller can be used to keep the components of the slurry from separating out. Alternatively, a chemical surfactant can be used to keep the particulate in suspension.

It is preferable that the system be cleaned after each use. In order to clean the oral care device, top 18 is removed from reservoir 16 (see FIG. 1). The reservoir is rinsed out with water, and then the reservoir is filled with water. The reservoir is tipped upside down and then switch 57 is pressed. This allows compressed air entering reservoir 16 to force water out of outlet 43, thus rinsing out the system downstream of outlet 43.

The head of the applicator can have a variety of configurations depending on the particular cleaning results desired. FIG. 5 is a sectional view of applicator 44 shown in FIG. 2. A flexible tube 62 extends through a handle 64. An on/off flow switch 66 includes a lever 68, spring 70 and pressure nub 72 that normally pinches the tube closed as shown in FIG. 5, thus stopping flow. When an operator presses lever 68, nub 72 is lifted off tube 62, allowing flow of the air, water and particulate. A quick disconnect 73 allows easy replacement of nozzle 74. The nozzle includes a neck 76 which allows easy access to all locations in the mouth.

FIGS. 6A and 6B disclose a replacement nozzle with a brush head having a brush head 78 with bristle tufts 79. FIGS. 7A and 7B disclose a replacement nozzle with a rubber cone 80 about a nozzle tip 82.

Figure 8:
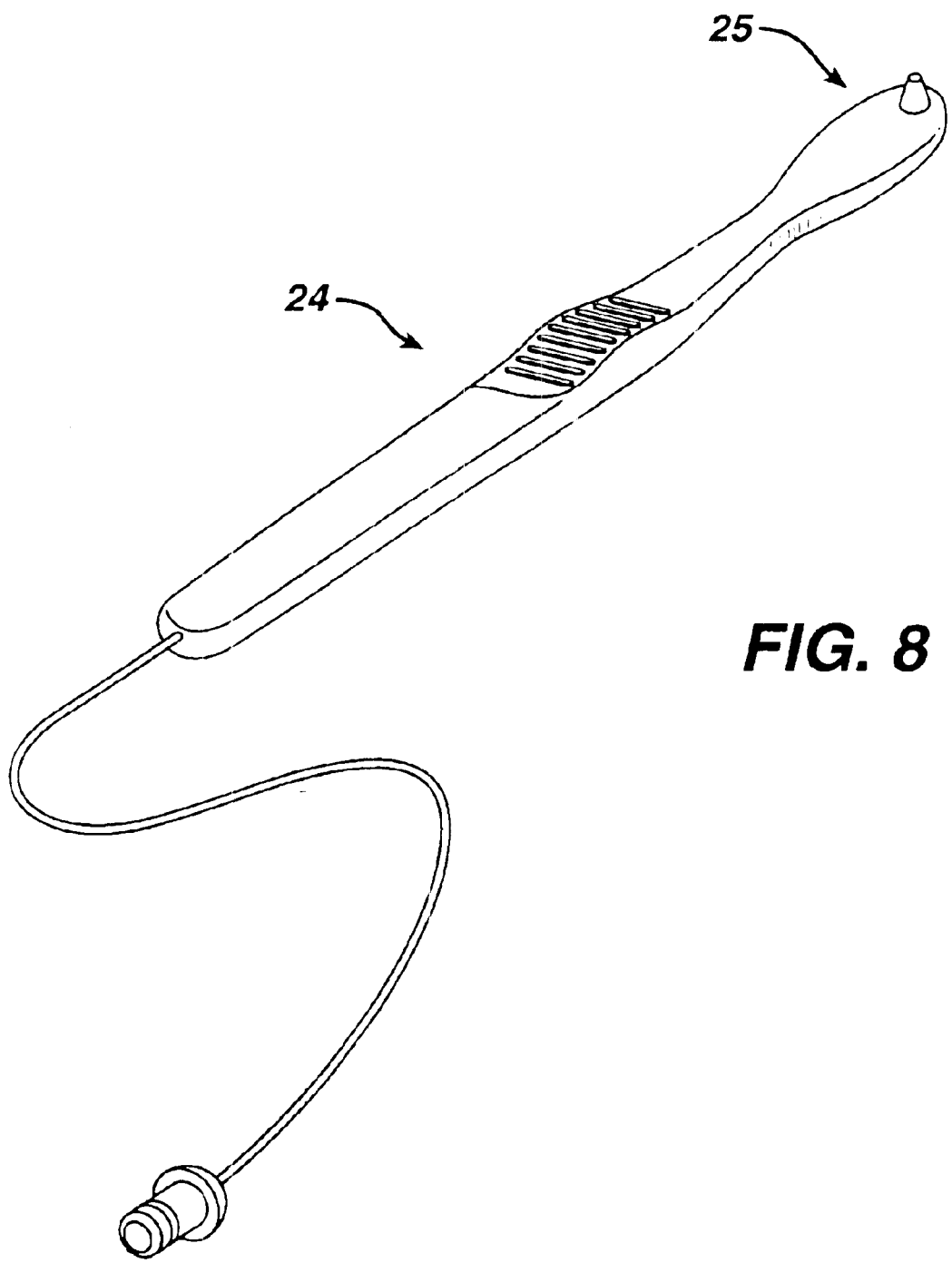
FIG. 8 is a perspective view of the applicator 24 of FIG. 4 with an alternative head design.

FIG. 8 discloses the applicator 24 of FIG. 4 with an alternative head design. Here the bristle tufts, manifolds and nozzles of FIG. 4 have been replaced by a single circular nozzle.

FIGS. 9A–E show various configurations of applicator heads. In FIG. 9A, an oval nozzle 84 is provided which can spray a broad pattern to cover relatively large tooth surfaces (e.g. the buccal face). A second circular nozzle 86 is provided and is slightly longer than nozzle 84, thus allowing nozzle 86 to reach between teeth. Nozzle 86 is surrounded by bristle tufts 88 which, among other things, provide a sensory guide to the user for the proper placement of the spray in the mouth. FIG. 9B is similar to FIG. 9A except that nozzle 84 has been removed and nozzle 86 is shorter.

FIG. 9C has a nearly full compliment of bristle tufts 90 with a single circular nozzle 92 located somewhat centrally on the head. FIG. 9D is similar to FIG. 9C except that the circular nozzle has been replaced with an oval nozzle that is located further towards the free end of the head. FIG. 9E is similar to FIG. 9D except that a large number of the bristle tufts have been removed.

Figure 10:
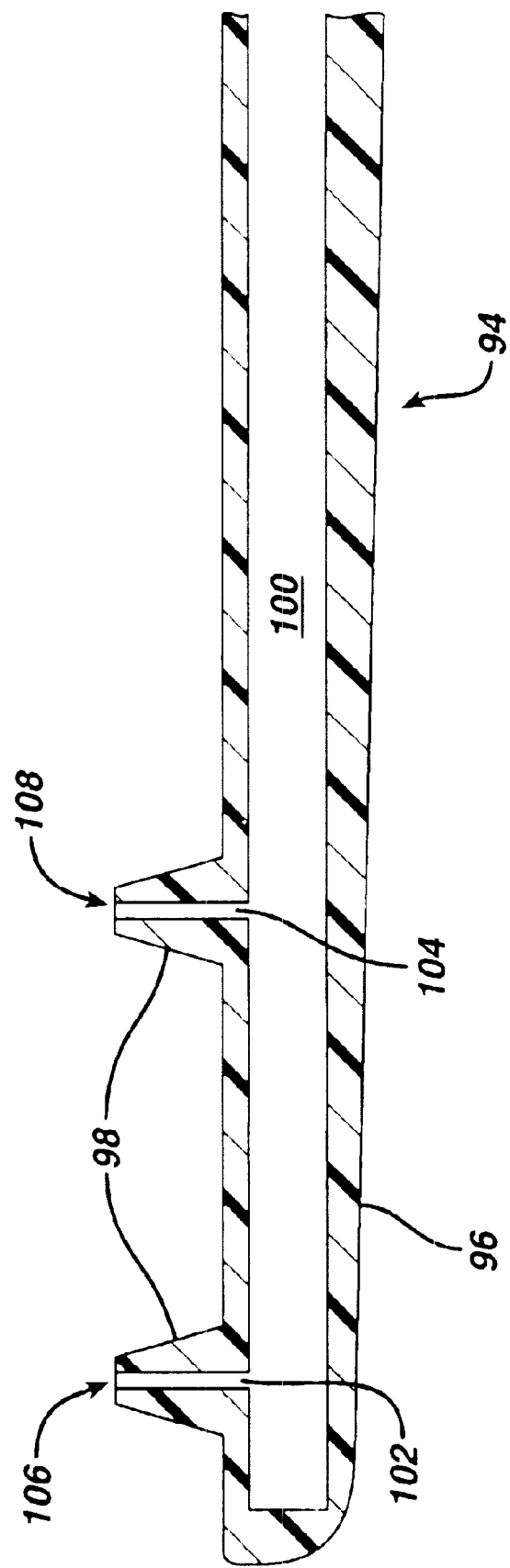
FIGS. 10 and 11 are partial sectional views of alternative designs for applicator heads.

FIG. 10 is a partial sectional view of an applicator 94 with a head 96. Two nozzles 98 are connected by a conduit 100 to the slurry reservoir (not shown). The air, water and particulate from the reservoir travels down the conduit to a pair of orifices 102 and 104 and then exits at nozzle tips 106 and 108 to provide a dual spray.

Figure 11:
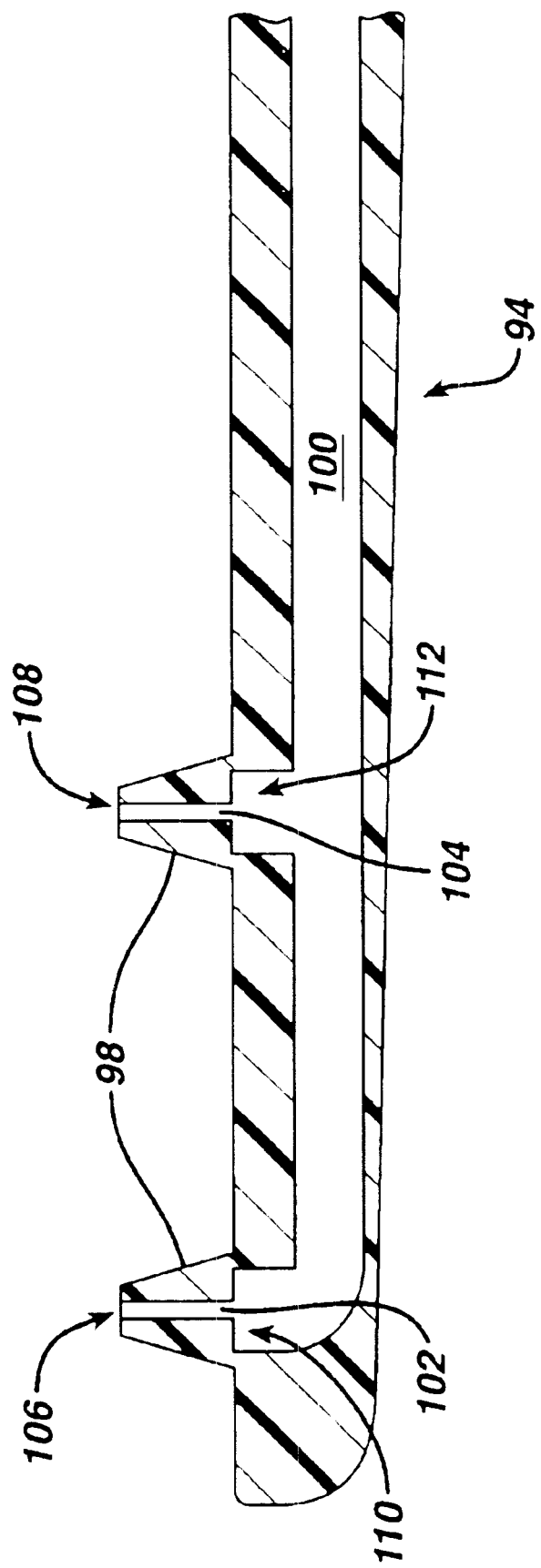

FIG. 11 is similar to FIG. 10 except that orifices 102 and 104 are connected respectively to conduit 100 by a pair of manifolds 110 and 112.

Figure 12:
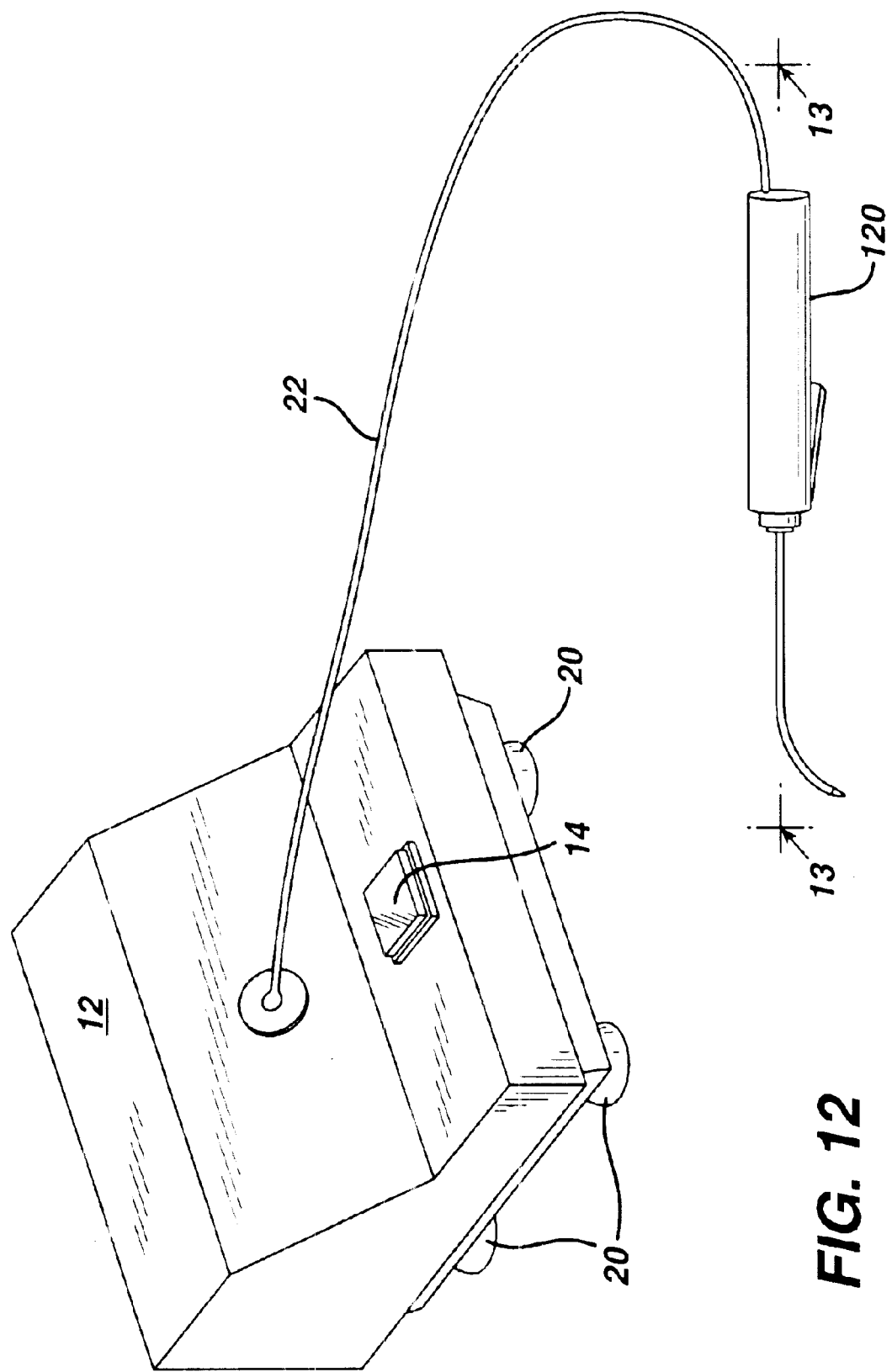
FIG. 12 is a perspective schematic view of an alternative embodiment oral care device.

FIG. 12 discloses an alternative embodiment oral care device. The main difference in this embodiment is that the slurry reservoir has been moved from being attached to housing 12 to within a handle 120 of the oral care device. As such, tube 22 is conducting just compressed air from the housing to handle 120.

Figure 13:
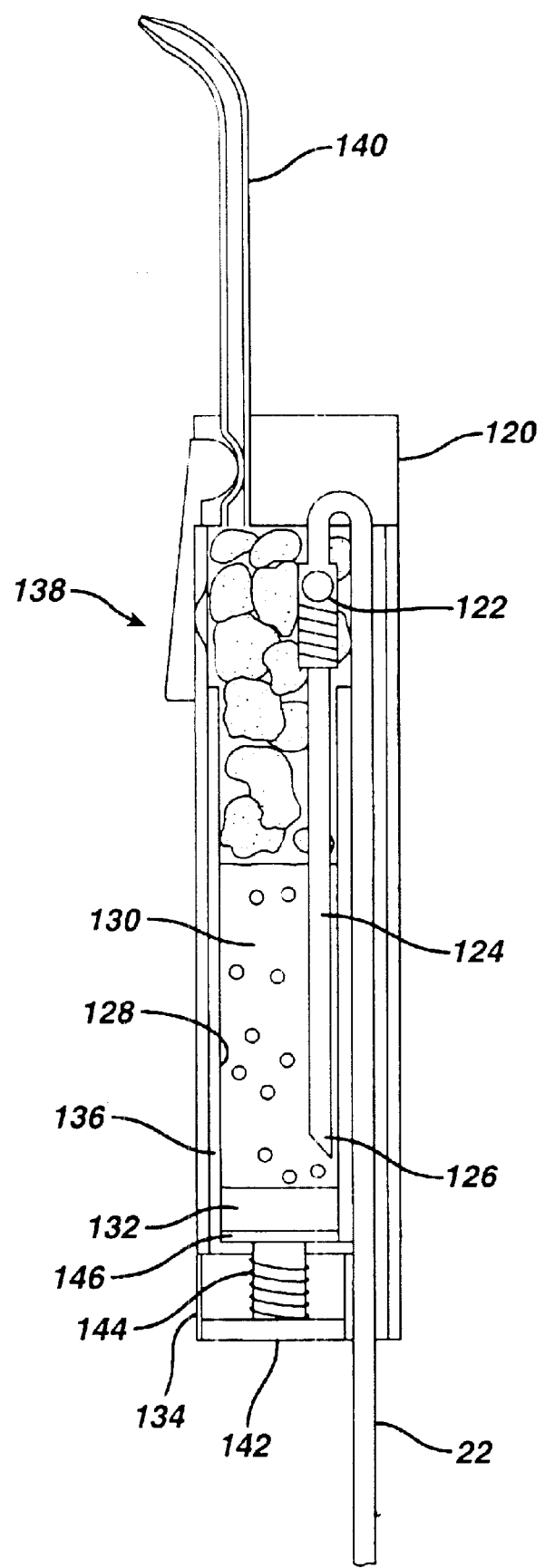
FIG. 13 is a sectional view of the handle/head of FIG. 12 taken along the lines 13—13.

Turning to FIG. 13, a sectional view of handle 120 is shown. Tube 22 enters the handle at one end, allowing compressed air to enter the handle. A check valve 122 operates the same as the check valve described above with reference to FIG. 3. After check valve 122, a rigid tube 124 further conducts compressed air within the handle. Tube 124 has a beveled end 126 the purpose of which will be explained below.

A flexible plastic bag 128 contains two chambers. A first chamber 130 contains a slurry while a second chamber 132 contains water. A new plastic bag containing the slurry and water is used each time the oral care device is operated to clean a person's oral cavity. To load the bag, a plunger cap 134 is unscrewed from an end of the handle. A ridge container 136 having no top or bottom is then removed from the handle. A new bag is placed in container 136, and the container is loaded back into the handle. As the container and bag are loaded, tip 126 of tube 124 punctures chamber 130 of the bag. When the bag is fully loaded into the handle, chamber 132 will not be punctured by tip 126. Cap 134 is then screwed back onto the end of the handle.

The device is then used to clean the oral cavity as described previously. Switch 14 on housing 12 is depressed to activate the air compressor. A switch 138, operating substantially the same as switch 66 described above, is depressed to allow air, water and particulate to flow under pressure to a head 140. A difference is that handle 120 should not be tipped too far away from its vertical orientation shown in FIG. 13. The vertical orientation keeps tip 126 submerged in the slurry. If the handle is tipped too much away from a vertical orientation, tip 126 may not be submerged in the slurry and the device will not operate properly.

When cleaning of the oral cavity is completed, the oral care device is cleaned as follows. Handle 120 is tipped upside down from its orientation in FIG. 13. A plunger 142 of cap 134 is pressed by the operator to force the cap towards head 140 against the resistance of a compression spring 144. Such motion causes a portion 146 of the plunger to press chamber 132 against tip 126, thus puncturing chamber 132. This allows water to exit bag 128 and be forced by compressed air out of handle 120 and head 140, thereby cleaning these components.

What is claimed is:

1. An oral care device, comprising:

a housing;

an electric motor within the housing;

an air compressor within the housing and operated by the motor;

a slurry;

an enclosed container, attached to the housing, for holding said slurry;

a first conduit for conducting compressed air from the compressor into the container; and a second conduit for conducting the slurry and air from the container to an applicator from which the slurry and air is sprayed into the oral cavity of a human, the slurry and air exiting the container at a location above a surface of the slurry.

2. The oral care device of claim 1, wherein the slurry includes water.

3. The oral care device of claim 1, wherein the slurry includes sodium bicarbonate and sodium laurel sulfate.

4. The oral care device of claim 1, further including an air ballast through which the first conduit passes, the ballast being located between the compressor and the container.

5. The oral care device of claim 4, wherein the ballast includes an adjustable valve which allows air to escape from the ballast, thereby controlling air pressure.

6. The oral care device of claim 4, further including an overpressure valve attached to the first conduit which will open if the air pressure exceeds a set pressure.

7. The oral care device of claim 1, wherein the slurry is a mixture of a cleaning powder and fluid in a ratio by volume of from about 1 part powder:10 parts fluid to 4 parts powder:10 parts fluid.

8. The oral care device of claim 1, wherein the first conduit conducts compressed air from the compressor to near the bottom of the container.

9. The oral care device of claim 1, wherein the slurry includes an additive selected from the group consisting of fluoride, an anti-bacterial agent, chlorhexadine, a sweetener, saccharine, a flavoring, mint, a desenstizer and triclosan.

10. An oral care device, comprising:

an electric motor;

an air compressor operated by the motor;

an enclosed container for holding a slurry;

a first conduit for conducting compressed air from the compressor into the container, the compressed air being at a pressure of between about 20 psi to about 50 psi; and a second conduit for conducting the slurry and air from the container to an applicator from which the slurry and air is sprayed into the oral cavity of a human, the slurry and air exiting the container at a location above a surface of the slurry, the second conduit being at least about 24 inches in length.

11. The oral care device of claim 10, wherein the compressed air is at a pressure of between about 25 psi to about 45 psi.

12. The oral care device of claim 10, wherein the compressed air is at a pressure of between about 30 psi to about 40 psi.

13. The oral care device of claim 10, wherein the compressed air is at a pressure of between about 32 psi to about 38 psi.

14. The oral care device of claim 10, wherein, the second conduit is at least about 30 inches in length.

15. The oral care device of claim 10, wherein, the second conduit is at least about 36 inches in length.

16. The oral care device of claim 10, wherein, the second conduit is at least about 42 inches in length.

17. The oral care device of claim 10, wherein the slurry is a mixture of a cleaning powder and fluid in a ratio by volume of from about 1 part powder:10 parts fluid to 4 parts powder:10 parts fluid.

18. The oral care device of claim 10, wherein the first conduit conducts compressed air from the compressor to near the bottom of the container.

* * * * *